US011077215B2

(12) United States Patent
Goldhawk et al.

(10) Patent No.: US 11,077,215 B2
(45) Date of Patent: Aug. 3, 2021

(54) CO-EXPRESSION OF MAGNETOTACTIC BACTERIAL GENES AND GENES ENCODING IRON HANDLING PROTEINS IN CELLS

(71) Applicant: Multi-Magnetics Incorporated, London (CA)

(72) Inventors: Donna E. Goldhawk, London (CA); D. James Koropatnick, London (CA); Rene Figueredo, London (CA); Frank S. Prato, London (CA); R. Terry Thompson, London (CA); Neil Gelman, London (CA)

(73) Assignee: Multi-Magnetics Incorporated, London (CA)

( * ) Notice: Subject to any disclaimer, the term of this patent is extended or adjusted under 35 U.S.C. 154(b) by 1158 days.

(21) Appl. No.: 15/121,653

(22) PCT Filed: Jul. 8, 2014

(86) PCT No.: PCT/CA2014/000555
§ 371 (c)(1),
(2) Date: Aug. 25, 2016

(87) PCT Pub. No.: WO2015/127527
PCT Pub. Date: Sep. 3, 2015

(65) Prior Publication Data
US 2016/0367706 A1  Dec. 22, 2016

Related U.S. Application Data

(60) Provisional application No. 61/944,146, filed on Feb. 25, 2014.

(51) Int. Cl.
| | | |
|---|---|---|
| C07K 14/195 | (2006.01) |
| A61K 49/18 | (2006.01) |
| C12N 15/85 | (2006.01) |
| C12Q 1/6883 | (2018.01) |
| C12Q 1/689 | (2018.01) |

(52) U.S. Cl.
CPC ........ *A61K 49/1896* (2013.01); *C07K 14/195* (2013.01); *C12N 15/85* (2013.01); *C12Q 1/689* (2013.01); *C12Q 1/6883* (2013.01); *C12N 2510/00* (2013.01)

(58) Field of Classification Search
None
See application file for complete search history.

(56) References Cited

U.S. PATENT DOCUMENTS

2013/0280173 A1* 10/2013 Neeman ............ A61K 49/14
424/9.34

OTHER PUBLICATIONS

Genove, G. et al., Nature Med., Mar. 2005, vol. 11: pp. 450-454.*
PcDNA 3.1 vector map and information, printed Feb. 3, 2020, 2 pages.*
Kolinko—Biosynthesis of Magnetic Nanostructures in a Foreign Organism by Transfer of Bacterial Magnetosome Gene Clusters—Nature Nanotechnology—Letters—Published Online: Feb. 23, 2014; DOI: 10.1038/NNAMO.2014.13.
Komeili, Arash; Molecular mechanism of compartmentalization and biomineralization in magnetotactic bacteria; Department of Plant an Microbial Biology, University of California, Berkeley, CA, USA; 2011 Federation of European Microbiological Societies; Published by Blackwell Publishing Ltd.
Staniland, Sarah; An accommodating host; A commercially viable method for synthesizing magnetic nanoparticles could be developed by transferring clusters of genes from magnetic bacteria to foreign, more stable bacteria; Nature Nanotechnology; vol. 9, Mar. 2014; www.nature.com/naturenanotechnology.
Komeili, A.; Molecular mechanisms of magnetosome formation; Annu Rev Biochem 76, 1-27 (2007).
Zurkiya, O. et al.; MagA is sufficient for producing magnetic nanoparticles in mammalian cells, making it an MRI reporter, Magn Reson Med 59, 1225-1231 (2008).
Benoit, M. et al.; Visualizing implanted tumors in mice with magnetic resonance imaging using magnetotactic bacteria, Clin Cancer Res 15, 5170-5177 (2009).
Goldhawk, D. et al.; Using the magnetosome to model effective gene-based contrast for magnetic resonance imaging, WIRES Nanomed Nanobiotechnol Epub ahead of print, doi: 10,1002/wnan, 1165 (2012).
Goldhawk, D. et al.; Magnetic resonance imaging of cells overexpressing MagA, an endogenous contrast agent for live cell imaging, Moi Imaging 8, 129-139 (2009).
Rohani, R. et al.; Imaging tumor growth non-invasively using expression of MagA or modified ferritin subunits to augment intracellular contrast for repetitive MR, Moi Imaging Biol, Epub ahead of print, doi. 10.1007/S11307-1103-10661-11308 (2013).
Anderson, C. et al.; Mammalian iron metabolism and its control by iron regulatory proteins, Biochem Biophys Acta 1823, 1468-1483 (2012).
Sengupta, A. et al.; Biophysical features of MagA expression in mammalian cells: implications for MRI contrast, Frontiers in Microbiotechnology, Ecotoxicology and Bioremediation, submitted (2013).
Lee, C. et al.; Transverse relaxation rate (R2) dependence on refocusing pulse interval (2tau) in MagA expressing breast/melanoma tumor cells, in World Molecular Imaging Conference, Abstract LBAP 129, Savannah, USA (2013).
(Continued)

*Primary Examiner* — Michael D Burkhart
(74) *Attorney, Agent, or Firm* — Ridout & Maybee LLP

(57) ABSTRACT

The invention provides an improved modified magnetosome that contains more iron therein with the combination of the expressed genes. This is achieved by co-expression of (a) one or more bacterial magnetotactic genes to amplify iron uptake, compartmentalization and biomineralization in cells, with (b) one or more mammalian iron handling proteins that together augment(s) and/or regulate the cells iron pool. As a result, mammalian cells or bacterial cells that are transfected or transformed, respectively, can be more effectively tracked using various imaging technologies.

8 Claims, 2 Drawing Sheets

(56) References Cited

OTHER PUBLICATIONS

Sengupta, A. et al.; MRI relaxation rates in tumour cells expressing the MagA reporter gene in International Society for Magnetic Resonance in Medicine Scientific Workshop on MRI-based Cell Tracking, Abstract 26, Miami, USA (2012).
Liu, L. et al.; Non-Invasively Targeting Myocardial Progenitor Cells for the Treatment of Duchenne Muscular Dystrophy-Related Cardiomyopathy using MRI/PET, in Stem Cell Network, Abstract accepted, Banff, Canada (2013).
Quiaoit, K et al.; MagA Reporter Gene Expression for Magnetic Resonance Imaging of Breast Carcinoma, in London Health Research Day, Biomedical Imaging & Engineering Abstract 33, London, Canada (2013).
Recalcati, S. et al.; Differential regulation of iron homeostasis during human macrophage polarized activation, Eur J Immunol 40, 824-835 (2010).
Pantopoulos, K. et al.; Mechanisms of mammalian iron homeostasis, Biochemistry 51, 5705-5724 (2012).
Braun, R.; When harmless bacteria go bad, Scienfic American (2013).
Ghajar, C. et al.; The perivascular niche regulates breast tumour dormancy, Nat. Cell Biol 15, 807-817 (2013).
Ihme, and Cohen, J.; Health metrics; A controversial close-up of humanity's health, Science 338, 1414-1416 (2012).
News (2013) World Diseases by the Numbers, Science 341, 325 (2013).
Makkar, R. et al.; Intracoronary cardiosphere-derived cells for heart regeneration after myocardial infarction (Caduceus): a prospective, randomised phase 1 trial, Lancet 379, 895-904 (2012).
Kroemer, G. et al.; Classification of cell death: recommendations of the Nomenclature Committee on Cell Death (2009), Cell Death Differ 16, 3-11.
Huang, X. et al.; Redox-active metals, oxidative stress, and Alzheimer's disease pathology, Ann NY Acad Sci 1012, 153-163 (2004).
Ferguson, RM et al,; Tailoring the magnetic and pharmacokinetic properties of iron oxide magnetic particle imaging tracers; KM.Biomed Tech (Berl) Dec. 2013; 58(6): 493-507.
International Search Report for corresponding PCT Patent Application No. PCT/CA2014/000555.
Written Opinion dated Oct. 14, 2014 for corresponding PCT Patent Application No. PCT/CA2014/000555.

\* cited by examiner

CO-EXPRESSION OF MAGNETOTACTIC BACTERIAL GENES AND GENES ENCODING IRON HANDLING PROTEINS IN CELLS

CROSS REFERENCE TO RELATED APPLICATIONS

This patent application is a U.S. nationalization under 35 U.S.C. § 371 of International Application No. PCT/CA2014/000555, filed Jul. 8, 2014, which claims the benefit of priority under 35 U.S.C. § 119(e) to U.S. Provisional Application Ser. No. 61/944,146, filed Feb. 25, 2014. The disclosures set forth in the referenced applications are incorporated herein by reference in their entireties, including all information as originally submitted to the United States Patent and Trademark Office.

FIELD OF INVENTION

The invention relates to the production of magnetosome-like structures in cells with increased iron storage. More specifically, the invention provides gene expression systems using a combination of magnetotactic bacterial gene(s) with mammalian genes involved in iron handling in order to augment a cell's iron pool. The invention further provides in vitro and in vivo imaging, diagnostic and therapeutic methods using cells co-expressing the resultant increased iron containing magnetosome-like structures in order to enhance iron contrast using a variety of imaging technologies.

BACKGROUND OF THE INVENTION

Non-invasive mapping of cellular or subcellular events in living organisms, or molecular imaging, is an evolving and largely unexplored field. Magnetic resonance imaging (MRI) is used for in vivo cellular imaging and requires the use of cellular contrast agents. While many of the current developments in contrast agents continue to revolve around SPIO (superparamagnetic iron oxide) particles, progress in the field of gene-based contrast is being recognized (6).

The bacterial, putative iron transport protein MagA has been implicated, among other proteins, in the formation of magnetosomes: membrane-enclosed vesicles that compartmentalize iron biominerals (1, 2). Magnetosomes are not toxic and impart magnetic properties to the cell that may be clinically useful (3, 4). Canadian patent application 2,655,118 (the disclosure of which is hereby incorporated by reference in its entirety) describes the use of magnetosome genes in eukaryotic cells, including MagA -derived iron contrast, for cell tracking using MRI.

There however, remains a need to improve the MR signal for a variety of clinical diagnostic and therapeutic applications.

SUMMARY OF THE INVENTION

The present invention provides a gene based iron contrast by the augmentation of a cell's iron pool. The present invention combines the use of magnetotactic genes that form magnetosome-like structures in cells with genes encoding iron handling proteins.

The invention in its broadest sense is the co-expression of (a) one or more bacterial magnetotactic genes to amplify iron uptake, compartmentalization and biomineralization in cells, with (b) one or more genes encoding iron handling proteins that together augment(s) and/or regulate the cells' iron pool. The invention provides an improved modified magnetosome that contains more iron therein with the combination of the expressed genes. More iron encompasses the aspect of amount as well as size of the iron biomineral produced and/or crystal structure all of which contribute to a better signal for imaging technologies. As a result, mammalian cells or bacterial cells that are transfected or transformed, respectively, can be more effectively tracked using various imaging technologies.

In a representative but non-limiting embodiment, the invention provides the co-expression of ferritin subunits (heavy and/or light chains) with one or more magnetotactic bacterial genes, including magnetosome genes such as but not limited to MagA, MamK and MMS16. The ferritin subunits are heavy (HF) and light subunits (LF) each of which lacks the iron response elements (IRE). In aspects, the ferritin subunits are mammalian, in aspects human.

The co-expression of one or more magnetotactic bacterial genes, and mammalian iron handling proteins such as modified human ferritin heavy and light subunits, each lacking iron response elements (IRE), promotes iron biomineralization and enhances cellular contrast for molecular imaging using any variety of techniques such as magnetic resonance imaging (MRI).

The invention thus provides enhancement and/or regulation of gene-based, iron contrast by augmenting a cell's iron pool, as for example stored by a modified form of ferritin, in addition to increasing iron uptake through for example the MagA transporter or other magnetotactic bacterial protein (s), including those associated with forming a magnetosome-like structure. The present invention addresses current limitations in cell tracking using exogenously-introduced iron particles, such as superparamagnetic iron oxide (SPIO) nanoparticles.

According to an aspect of the present invention is a plasmid comprising (a) one or more bacterial magnetotactic genes to amplify iron uptake, compartmentalization and biomineralization in cells in combination with (b) one or more iron handling proteins that together augment(s) and/or regulates the cells' iron pool. In aspects, the iron handling proteins may be of mammalian origin.

According to another aspect of the present invention is an expression system comprising one or more magnetotactic genes and one or more mammalian genes encoding iron handling proteins under the control of one or more suitable promoters. The one or more magnetotactic genes may be provided as an operon.

According to a further aspect of the invention is a double or triple gene expression system comprising a magnetotactic bacterial gene and modified human heavy and/or light ferritin subunits lacking iron response elements (IRE). In aspects, the iron response element is deleted from the 5' untranslated region of the human heavy and light ferritin gene. The gene expression system is provided as a construct for transfection into a variety of eukaryotic and prokaryotic cell types including mammalian cells, human or animal as well as bacterial cells. The mammalian cells may be of any type and are not limited and may include any type of cell such as stem cells and the like as is understood by one of skill in the art.

In aspects the entire iron response element is deleted or a portion thereof, the portion being sufficient to lack the expression of the IRE as is understood by one of skill in the art.

According to an aspect of the invention is a cell transfected with a gene construct comprising a magnetotactic bacterial gene and modified human heavy and/or light ferritin subunits lacking iron response elements (IRE). In aspects, the magnetotactic bacterial gene is a MagA gene.

According to an aspect of the invention is a cell transfected with a gene construct comprising MagA and modified human heavy and/or light ferritin subunits lacking iron response elements (IRE) in the 5' untranslated regions. The cell can be mammalian or bacterial.

According to an aspect of the present invention is a dual expression system where the same promoter element induces magnetotactic bacterial gene(s), including magnetosome gene(s), and mammalian genes encoding iron handling proteins. Those skilled in the art will recognize that this inducible expression may be engineered to respond to antibiotic stimulation or a specific cellular transcription factor, as in reporter gene expression. It is understood that a single cell may be engineered to express multiple genes.

According to another aspect of the present invention is the constitutive expression of one set of genes and inducible expression of additional gene(s).

According to a further aspect of the present invention is a method for making a cell that co-expresses one or more magnetotactic bacterial genes and mammalian modified ferritin heavy and light subunits, the method comprising; transfecting a cell with a construct comprising one or more magnetotactic bacterial genes and genes encoding modified ferritin heavy and light subunits under the control of an inducible promoter.

According to an aspect of the present invention is a method for making a cell that co-expresses MagA and modified ferritin heavy and light subunits lacking the IRE (iron responsive element), the method comprising; transfecting a cell with a construct comprising MagA and modified ferritin heavy and light subunits lacking the IRE in the 5' untranslated region of the heavy and light gene under the control of a suitable inducible promoter.

According to an aspect of the present invention is the detection of multiple contrast genes using MRI and MPI imaging platforms as well as hybrid imaging platforms, such as PET/MRI (4, 11), SPECT/MRI, PET/SPECT/MRI, PET/CT, SPECT/CT, bioluminescence tomography (BLT)/MRI, BLT/CT, BLT/PET, BLT/PET/MRI (12) and MPI. Those skilled in the art will recognize that non-invasive imaging methods and hardware are adaptable to multiple applications.

According to another aspect of the present invention is the inducible expression of magnetotactic bacterial gene(s), including magnetosome gene(s), and mammalian genes encoding iron handling proteins, like HF and/or LF genes, by two or more distinct promoters. Thus more than one gene may be monitored at the same time and the simultaneous expression will provide the maximal or distinct MR contrast signal.

A beneficial feature of the present invention is the fact that the genetically altered cells of the invention can continue to express and produce magnetosome-like structures and HF and/or LF in vivo during growth, differentiation and replication of the cell. As a result, such cells can be visually tracked as they grow, differentiate and replicate inside a host without dilution of the genetically-programmed contrast agents. Therefore, these structures provide long-term in vivo contrast agents in a wide variety of cells, tissues, organs, etc. With respect to the genetically altered cells being bacterial cells, these can be transformed in vitro or ex vivo with the expression systems of the invention and reintroduced into the gut in order to provide an in vivo contrast in the gastrointestinal tract.

The expression systems of the invention may in embodiments comprise MagA and modified heavy and light ferritin subunits lacking iron response elements and be used in eukaryotic cells, such as mammalian cells. The cells may be stem cells or the construct may be used for transfection into tissues.

The construct in cells and tissues may be imaged using magnetic resonance imaging (MRI) or magnetic particle imaging (MPI) alone or in combination with other imaging modalities, such as positron emission tomography (e.g., PET/MRI or PET/MPI) or single photon emission computed tomography (e.g., SPECT/MRI or SPECT/MPI).

According to an aspect of the invention there is provided an expression system for augmenting and/or regulating iron levels in cells, said expression system comprising (a) one or more bacterial magnetotactic genes to amplify iron uptake, compartmentalization and biomineralization in cells, and (b) one or more iron handling proteins, wherein (a) and (b) are under control of one or more promoters and, optionally, one or more selection markers.

According to a further aspect is a mammalian cell transfected with a plasmid comprising MagA and mammalian ferritin heavy and light subunit genes lacking the IRE in the 5' untranslated regions under control of one or more promoters and, optionally, one or more selection markers.

According to a further aspect is a method for making a cell that co-expresses one or more magnetotactic bacterial genes and modified ferritin heavy and light subunits, the method comprising; transfecting a cell with a construct comprising one or more magnetotactic bacterial genes and modified ferritin heavy and light subunits under the control of an inducible promoter.

According to a further aspect is method for making a cell that co-expresses MagA and modified ferritin heavy and light subunits lacking the IRE, the method comprising; transfecting a cell with a construct comprising MagA and modified ferritin heavy and light subunits lacking the IRE in the 5' untranslated region of the heavy and light genes under the control of a suitable inducible promoter.

According to another aspect is a method for producing a magnetosome-like structure comprising increased amounts of iron contained therein, the method comprising cultivating a transformed cell according to any one of claims 22 to 26 under conditions suitable to effect expression of the genes contained therein.

According to another aspect is a DNA construct for expression of multiple gene products in a cell leading to augmented iron levels, the construct comprising: (a) one or more promoters located at the 5' end of the construct, which is operable in a cell, (b) one or more bacterial magnetotactic genes, (c) one or more mammalian iron handling proteins, and (d) a 3' transcription termination sequence comprising a polyadenylation signal following the protein coding sequences.

Any of the constructs of the invention as described herein encompass promoters selected from the group consisting of inducible promoters, constitutive promoters and tissue specific promoters.

According to another aspect is a modified breast cancer cell co-expressing MagA and ferritin heavy and light subunits modified to lack an iron response element (IRE), wherein said modified breast cancer cell contains a higher amount of iron than a matched unmodified breast cancer cell.

According to a further aspect is a method for detecting changes in cellular iron, the method comprising co-expressing a magnetotactic bacterial gene and a eukaryotic iron handling gene in a cell and monitoring said cell using an imaging method.

According to a further aspect is a method for tracking cancer growth and/or metastasis, the method comprising co-expressing a magnetotactic bacterial gene and a eukaryotic iron handling gene in a cancer cell and monitoring said cell using an imaging method.

According to a further aspect is a method for monitoring cardiac stem cell transplantation, the method comprising co-expressing a magnetotactic bacterial gene and a eukaryotic iron handling gene in a cardiac stem cell and monitoring said cell using an imaging method.

According to a further aspect is a method for tracking neurodegenerative disease, the method comprising co-expressing a magnetotactic bacterial gene and a eukaryotic iron handling gene in a neural cell and monitoring said cell using an imaging method.

According to a further aspect is a method for tracking internal bacteria, the method comprising co-expressing a magnetotactic bacterial gene and a eukaryotic iron handling gene in a bacterial cell and monitoring said cell using an imaging method.

According to a further aspect is modified cell co-expressing one or more magnetosome genes and one or more iron handling genes, wherein said modified cancer cell contains a higher amount of iron than a matched unmodified cell.

The foregoing has broadly outlined the features and technical advantages of the present invention in order that the detailed description of the invention that follows may be better understood. Additional features and advantages of the invention will be described hereinafter which form the subject of the claims of the invention. It should be appreciated by those skilled in the art that the specific embodiment disclosed herein may be readily utilized as a basis for modifying or designing other structures for carrying out the same purposes of the present invention. It should also be realized by those skilled in the art that such equivalent constructions do not depart from the scope of the invention. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

The modified ferritin subunits (HF and/or LF) lack the noncoding regulatory IRE sequences; therefore, this modified form of ferritin is not subject to control by IRP.

DETAILED DESCRIPTION OF THE INVENTION

The invention provides for co-expression of (a) one or more bacterial magnetotactic genes to amplify iron uptake, compartmentalization and biomineralization in cells, with (b) one or more genes encoding iron handling proteins that together augment(s) and/or regulate the cells' iron pool. The invention provides an improved modified magnetosome that contains more iron or distinct iron biomineral therein with the combination of the expressed genes. As a result, mammalian cells or bacterial cells that are transfected or transformed, respectively, can be more effectively tracked using various imaging technologies.

As used herein "a higher amount of iron" may encompass one or more of a quantified amount, the size of the iron biomineral produced and the crystal structure of the iron biomineral produced by the present invention.

The invention is achieved by way of an expression vector (an expression construct) that is a plasmid or virus in which the one or more bacterial magnetotactic genes and the one or more genes encoding iron handling proteins are introduced into a target cell, to commandeer the cell's mechanism for protein synthesis to produce a magnetosome-like structure containing higher levels of iron or a unique iron biomineral. The plasmid further comprises regulatory sequences that act as enhancer and promoter regions and lead to efficient transcription of the gene(s) carried on the expression vector. The expression vector as described herein will produce a significant amount of stable messenger RNA, and therefore proteins.

The term "gene" will include the use of the gene, functional fragments thereof or cDNA. One of skill in the art would also understand that codon optimization may be used with respect to the genes discussed herein to determine and obtain optimal expression for a particular cell type whether eukaryotic or bacterial. In codon optimization an appropriate DNA sequence is synthesized specifically to efficiently express the mammalian gene in bacteria for example by first finding out which codons are the most widely used in the species of interest, and synthesize a DNA sequence made up of these. Various commercial programs are available and widely used for such purpose.

Figure 2:
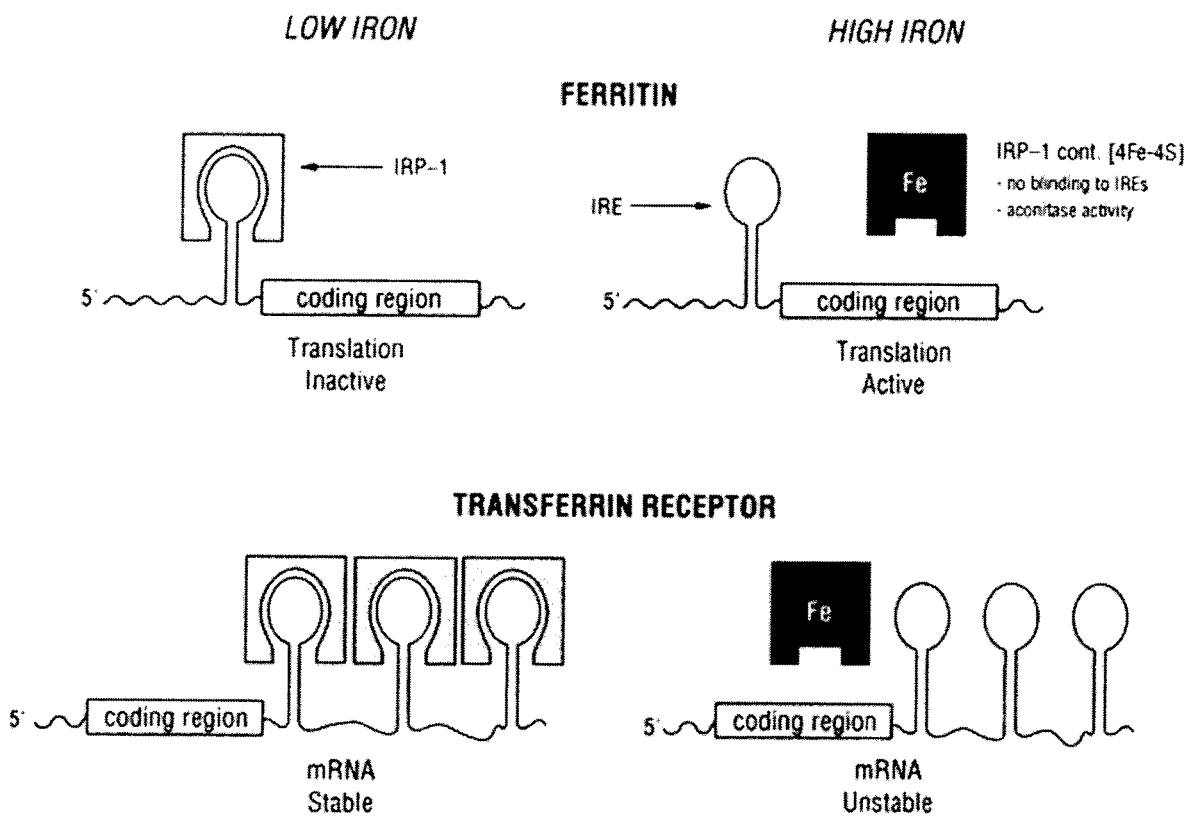
FIG. 2 shows how iron response elements regulate the expression of ferritin subunits. The iron response element (IRE) is a hairpin loop structure in the 5' noncoding sequences of the mRNA of ferritin heavy and light subunits. Under low cellular iron conditions, when the cell needs to release more iron from storage, ferritin synthesis is downregulated by the interaction of iron response protein (IRP) with the IRE. Iron uptake is increased by stabilizing the synthesis of transferrin receptor mRNA, through IRP-IRE interactions in the 3' noncoding sequence of the transferrin receptor transcript. The reverse is true when cellular iron is high and the cell needs to store more iron and downregulate iron import (Ponka and Lok (1999) The transferrin receptor: role in health and disease. Int J Biochem Cell Biol 31, 1111-37).

Suitable magnetotactic bacterial genes for use in the present invention may be selected from magnetosome genes MagA, MamK, MMS16 and also those encoded on a magnetosome genomic island and organized into operons such as the magnetosome membrane operons MamAB (17 genes including MamA/Mam22, MamB, MamE, MamJ, MamK, MamM, MamN, MamO, MamP), MamGFDC (4 genes including MamC/Mms13, MamG, MamD, MamF), MamXY (4 genes), the magnetic particle membrane specific operon Mms6 (5 genes including Mms6, Mms16, Mms24), the monocistronic MamW, and genes located outside the magnetosome genomic island, such as ChpA and those on the magnetotaxis operon MtxA and the magnetosome membrane operon MmeA (Kolinko, I., LohBe, A., Borg, S., Raschdorf, O., Jogler, C., Tu, Q., Posfai, M., Tompa, E., Plitzko, J., Brachmann, A., Wanner, G., Muller, R., Zhang, Y., and Schuler, D. (2014) Biosynthesis of magnetic nanostructures in a foreign organism by transfer of bacterial magnetosome gene clusters, *Nat Nanotechnol* 9, 193-197). Combinations of any of these genes and operons are envisaged in the invention. While bacterial operons are not normally expressed in mammalian cells, the multiple genes can be expressed each under control of its own promoter and selection marker. In this embodiment a single transient transfection can be done or multiple sequential transfections. These magnetotactic genes are utilized to amplify iron biomineralization in cells, in combination with the mammalian genes such as those encoding ferritin overexpression that is not subject to regulation by the iron response elements (FIG. 2). These reporter gene constructs for use in MRI, permit high resolution molecular imaging and non-invasive, in vivo tracking of cellular and molecular events.

Suitable genes encoding iron handling proteins may be selected from the group consisting of ferritin heavy and light subunits lacking the IRE and any protein subject to IRE regulation. Representative proteins include the transferrin receptor (UniProt P02786), transferrin (Transferrin St. Edward's University. 2005-07-18. Retrieved 2009-04-24; Yang F, Lum J B, McGill J R, Moore C M, Naylor S L, van Bragt P H, Baldwin W D, Bowman B H (May 1984). "Human transferrin: cDNA characterization and chromosomal localization". *Proceedings of the National Academy of Sciences of the United States of America* 81 (9): 2752-6. doi:10.1073/pnas.81.9.2752. PMC 345148. PMID 6585826), Iron Response Proteins (IRP) 1 and 2 (UniProt P21399; Samaniego F, Chin J, Iwai K, Rouault T A, Klausner R D (December 1994). Molecular characterization of a second iron-responsive element-binding protein, iron regulatory protein 2. Structure, function, and post-translational regulation". *J. Biol. Chem.* 269 (49): 30904-10. PMID 7983023), ferroportin (UniProt Q9NP59 and Q9JHI9), DMT1 (UniProt P49281), STEAP3 (UniProt Q658P3) and hepcidin (UniProt P81172). In aspects of the invention the genes may be mammalian as is understood by one of skill in the art.

Ferritin is a protein of 450 kDa consisting of 24 subunits that is present in every cell type. In vertebrates, these subunits are both the light (L) (UniProt 02792) and the heavy (H) type (UniProt P02794) with an apparent molecular weight of 19 kDa or 21 kDa respectively; their sequences are about 50% homologous. Ferritin genes are highly conserved between species. All vertebrate ferritin genes have three introns and four exons. The tyrosine residue at amino acid position 27 in the H subunit is thought to be associated with biomineralization.

The expression systems of the present invention can be used with any type of eukaryotic and prokaryotic cell. One of skill in the art would understand that the invention is applicable to eukaryotes in general, birds, plants, fungi, insects, fish, yeast, amphibians, reptiles, and invertebrates such as insects. In aspects the eukaryotic cells are mammalian, and may be human or animal. Mammalian cells may include for example cancer cells, nerve cells, muscle cells, cardiac cells, epithelial cells, adipocytes and stem cells. The expression systems of the present invention may also be used with prokaryotic cells, that is bacterial cells. Bacterial cells that are native to the gut of mammals can also be transformed with the expression systems of the present invention. Suitable bacteria may belong to the genera *Bacteroides, Clostridium, Fusobacterium, Eubacterium, Ruminococcus, Peptococcus, Peptostreptococcus, Bifidobacterium, Escherichia* and *Lactobacillus*. In this embodiment, the gastrointestinal tract of a mammal can be effectively imaged when the transformed bacteria are reintroduced into a mammal's gut.

Suitable promoters for use in the present invention are generally known in the field of molecular biology and may include inducible promoters, constitutive promoters and tissue specific promoters as is understood by one of skill in the art. Viral promoters may be chosen from, for example, cytomegalovirus (CMV; human immediate early), *Rous sarcoma* virus (RSV), simian virus 40 (SV40), and the long terminal repeat from Moloney murine leukemia virus (LTR). Mammalian promoters may be chosen from, for example, the elongation factor (EF) 1 a promoter, widely useful in mammalian cells; the cytokeratin 18 (K18) promoter; the cytokeratin 19 (K19) promoter; the tissue kallikrein promoter (Kall); the amylase promoter (AMY); and rat aquaporin-5 (rAQP5). In addition to these promoters that provide constitutive expression, the invention covers the use of more selective promoters that respond to particular cellular transcription factors, such as the minimal NIS (sodium iodide symporter) promoter that responds to Nkx2.5 (Dentice et al. (2004), *Mol Cell Biol* 24, 7863-7877). The combination of genes expressed to produce a magnetosome-like structure may be regulated by different promoters, constitutive or selective.

The invention as incorporated into plants and plant cells, one of skill in the art understands that several plant expression vectors are based on the Ti plasmid of *Agrobacterium tumefaciens*, where DNA to be inserted into plant is cloned into the T-DNA, a stretch of DNA flanked by a 25-bp direct repeat sequence at either end, and which can integrate into the plant genome. The T-DNA also contains the selectable marker. The *Agrobacterium* provides a mechanism for transformation, integration of into the plant genome, and the promoters for its vir genes may also be used for the cloned genes. Plant viruses may be used as vectors when *Agrobacterium* is not suitable for use in a specific plant. Examples of plant virus that can be used are the tobacco mosaic virus (TMV), potato virus X, and cowpea mosaic virus. The protein may be expressed as a fusion to the coat protein of the virus and is displayed on the surface of assembled viral particles, or as an unfused protein that accumulates within the plant. Expression in plant using plant vectors is often constitutive, and a commonly used constitutive promoter in plant expression vectors is the cauliflower mosaic virus (CaMV) 35S promoter.

Eukaryotic expression systems employing insect cell hosts are based upon one of two vector types: plasmid or plasmid-virion hybrids, the latter being most commonly used. The typical insect host is the common fruit fly, *Drosophila melanogaster*, however, other insect hosts include mosquito (*Aedes albopictus*), fall army worm (*Spodoptera frugiperda*), cabbage looper (*Trichoplusia ni*), salt marsh caterpillar (*Estigmene acrea*) and silkworm (*Bombyx mori*). In most all cases, heterologous protein overexpression occurs in suspension cell cultures. The exception, and one of the advantages of plasmid-virion systems, is that the recombinant virus may also be injected into larval host hemocel or literally fed to the mature host.

Plasmid-based vector systems provide a mechanism for both transient and long-term expression of recombinant protein and are commercially available such as the Drosophila Expression System (DES) (Invitrogen™). The transfection of competent D. melanogaster cells with engineered plasmid will mediate the transient (2-7 days) expression of heterologous protein. Establishing transformed cells that will express protein for longer time periods requires that the host cells be cotransfected with a "selection" vector, resulting in the stable integration of the expression cassette into the host genome. Constitutive expression is mediated using the Ac5 Drosophila promoter, whereas a metallothionein promoter guides copper-inducible expression. The DES vectors are designed with multiple cloning sites for insertion of the heterologous protein gene in any of three reading frames. A choice of vectors also provides for the expression of a variety of C-terminal fusion tags: V5 epitope for identification of expressed protein with V5 epitope antibody, polyhistidine peptide for simplified purification with metal chelate affinity resin, and the BiP secretion leader peptide.

To amplify cellular iron storage for the purpose of biomineralization, in one non-limiting limiting embodiment of the present invention MagA was overexpressed in combination with a dysregulated form of ferritin. In the absence of the IRE, ferritin does not respond to cellular iron binding proteins 1 and 2, thereby circumventing a key step in iron homeostasis: regulation of iron storage through receptor-mediated uptake by the interaction of transferrin, transferrin receptor and ferritin. Hence the absence of IRE allows greater flexibility in the control of iron levels and biominerals by magnetotactic bacterial genes.

The invention provides genetically engineered cells that produce magnetosome-like structures and HF and/or LF iron storage, as contrast agents for mapping and/or imaging of organs, tissues, cells, sub-cellular structures, proteins and peptides in living organisms both in vivo and in vitro. The method of the invention genetically alters cells to enhance iron storage in HF and/or LF and produce magnetosome-like structures as dense core vesicles that form MR contrast agents in the cell. The invention also provides genetic constructs from magnetotactic bacterial genes, including those of the magnetosome, and from mammalian genes, such as HF and/or LF, that may be expressed from vectors bearing inducible promoters or encoding other useful genes for targeting cells or for therapeutic treatments that can be followed by functional imaging or long-term tracking of transfected cells.

It is herein demonstrated that the magnetotactic bacterial gene and putative iron transporter, MagA, enhances MR contrast in iron-supplemented cells and in tissue formed from transplanted MagA-expressing cells. The MR contrast has been compared in clonal lines of MagA expressing cells to those expressing ferritin heavy and light chains, lacking iron response elements (HF and/or LF). The transverse relaxation rates, R2' in particular, are sensitive to cellular iron content. Changes in this MR parameter may be used to quantify cellular iron and improve the specificity of detection. The relationship between R2 and inter-echo time is investigated to improve cellular detection of iron using molecular MRI.

Figure 1:
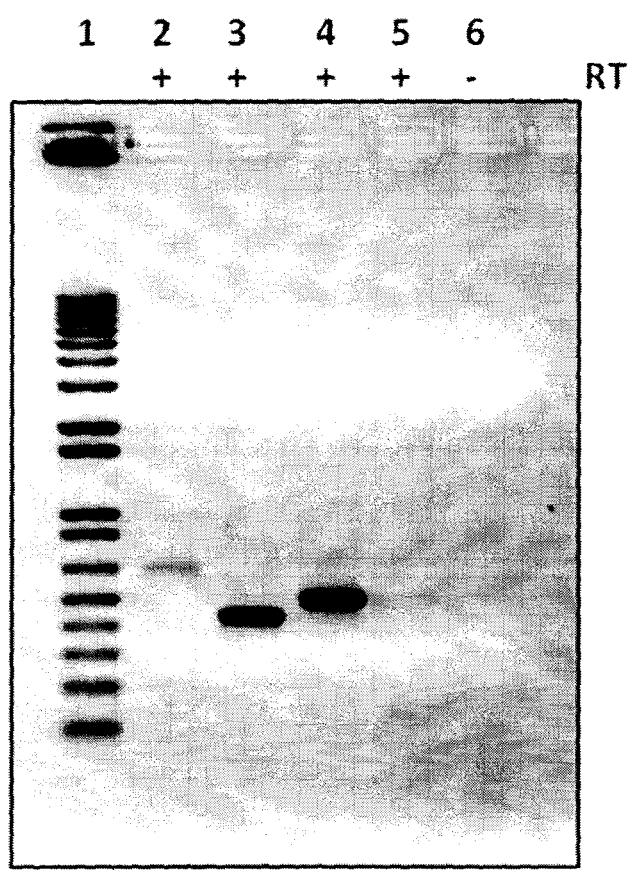
FIG. 1 shows RT-PCR of MDA-MB-435 cells expressing MagA and modified ferritin subunits HF+LF. Transcripts were amplified from 1 µg of total RNA, isolated from stably-expressing cells (clone 12), by reverse transcription (RT). The polymerase chain reaction (PCR) was performed on 4 µl RT, using 60° C. for the annealing temperature and 35 cycles. Ethidium bromide staining of complimentary DNA (cDNA) separated on a 1% agarose gel shows the product amplified with MagA primers (lane 2, 650 bp), HF primers (lane 3, 450 bp), LF primers (lane 4, 500 bp) and âactin primers (lane 5, 150 bp). Lane 6 contains an RT negative control for α-actin. Lane 1 contains a 1 Kb DNA ladder (Life Technologies).

The present invention demonstrates the triple expression system/construct of the present invention for use to further augment MR contrast (FIG. 1, Table 1).

The invention encompasses various expression strategies for magnetotactic bacterial, magnetosome and mammalian genes like the modified ferritin genes. Since each set of genes may provide contrast in the context of mammalian cell expression, they may operate independently and in an additive manner. Thus the possibility of distinct MR signatures are encompassed and within the scope of the invention for all types of genes and cells selected.

The invention has particular use with eukaryotic cells that express and overexpress one or more magnetotactic bacterial and/or magnetosome proteins as magnetosome-like structure contrast agents, in combination with mammalian genes like HF and/or LF for iron storage, permitting in vivo MRI, MPI, hybrid MR or x-ray imaging studies to follow the localization, proliferation, and long-term tracking of iron loaded cells. These cells may be tissue specific and permit non-invasive in vivo imaging of specific physiological or molecular functions.

Imaging systems that can be used with the present invention include at least the following, which can also be used in combination: positron emission tomography (PET), magnetic resonance imaging (MRI), gamma-ray imaging camera (GREI-II), computer tomography (CT), Single photon emission computed tomography (SPEC), bioluminescence tomography (BLT) and magnetic particle imaging (MPI). Magnetic particle imaging (MPI) is a new modality for imaging distributions of iron oxide nanoparticle tracers in vivo with good contrast, high sensitivity, and good spatial resolution, and thus is promising for clinical imaging in angiography and oncology. MPI requires high-quality iron oxide nanoparticle tracers with tailored magnetic and surface properties to achieve its full potential. Thus this technique is suitable for use with the presently claimed invention.

The present invention has further wide potential clinical uses such as, but not limited to, those described below.

Detecting Changes in Cellular Iron

Mammalian cells change their iron requirements to meet a given physiological need in both health (13) and disease (14). We demonstrate that both MagA and HF and/or LF expression respond to changes in extracellular iron while cellular iron homeostasis, as measured by changes in the level of transferrin receptor, appears intact. Expression of MagA and HF and/or LF may be utilized as sensors of changes in physiological iron levels.

Using MR detection methods, such as transverse relaxation rates, changes in cellular iron levels and iron biomineralization may be measured using a combination of magnetotactic bacterial genes, such as MagA, including magnetosome genes, and HF and/or LF. This provides a noninvasive tool for assessing the iron status of a given cell type.

The onset of changes in iron uptake or export and monitoring fluctuations in iron handling may be tracked by expressing a combination of magnetotactic bacterial genes, like MagA, including magnetosome genes, and HF and/or LF. Since transverse relaxation rates are a quantifiable measure of MR contrast and are related to cellular iron content, fluctuations in cellular iron throughout the cell's life cycle may be monitored.

Iron biomineralization may be amplified in mammalian cells, using a combination of magnetotactic bacterial genes, like MagA, including magnetosome genes, and HF and/or LF. This amplification of gene-based iron contrast will improve MR detection of cells without introducing cytotoxicity or altering endogenous cellular programming.

Under circumstances where altering the cell's iron handling abilities is desirable, a combination of magnetotactic bacterial genes, like MagA, including magnetosome genes, and HF and/or LF may be genetically engineered in the cell in order to introduce changes in iron handling. Such changes may influence the cell's labile iron pool and iron import, storage and export by creating a magnetosome-like compartment. Synthesis of a magnetosome-like structure may be genetically associated with a cellular function, reflecting an endogenous activity or overexpression of a desired macromolecule.

Bacteria harboring a combination of magnetotactic bacterial genes, like MagA, including magnetosome genes, and HF and/or LF may interact with mammalian cells and localize to sites within the body, such as the gut. This interaction may be detected by MRI or its hybrid modalities and signal the onset of a physiological process, be it in health or illness. This type of interaction has been identified as inter-kingdom signalling (15).

Tracking Cancer Growth and Metastasis

Cancer cells generally consist of a proliferative phenotype; however, dormant cancer cells may assume a quiescent state until reactivated by a stimulatory signal. It will be possible to use the combination of magnetotactic bacterial genes, like MagA, including magnetosome genes, and HF and/or LF to track the changes in cancer cell activity.

a) Many transplanted cancer cells will form tumour xenografts in animal models (6). A combination of magnetotactic bacterial genes, like MagA, including magnetosome genes, and HF and/or LF may be used to monitor tumour growth and metastasis in tumour xenografts using MRI.

b) P19 cells are a mouse embryonic carcinoma with stem cell characteristics and will differentiate into each of the 3 tissue types: endoderm, mesoderm and ectoderm. Introduction of a combination of magnetotactic bacterial genes, like MagA, including magnetosome genes, and HF and/or LF may be used to monitor cancer cell differentiation by MRI and better understand stem cell activity (11). Using this method, features of cancer stem cell activity such as the fraction of cells that differentiate in response to a given stimulus can be monitored.

c) Using specific promoters to drive contrast gene expression, transcription factor activities will be examined that are important in a given type of cancer. For example, a combination of magnetotactic bacterial genes, like MagA, including magnetosome genes, and HF and/or LF may be expressed to monitor Nkx2.5 activity by reporter gene expression (12). This method will also permit simultaneous tracking of more than one oncoprotein activity by using different promoters for each reporter gene involved in generating MR contrast.

d) One of the advantages of non-invasive imaging is the ability to investigate environmental cues of tumour formation within an in vivo context (16). Expressing a combination of magnetotactic bacterial genes, like MagA, including magnetosome genes, and HF and/or LF may be used to examine the context of tissue-specific tumour growth and metastasis. This method will combine the superior anatomy of MRI with molecular function and reveal the similarities and differences in cancer growth among transformed cell types and target organs.

e) Combinations of magnetotactic bacterial genes, like MagA, including magnetosome genes, and HF and/or LF may be expressed in cells derived from primary tumours to non-invasively track growth and metastasis of human disease in orthotopic animal models. This will provide a measure of personalized medicine for developing therapies and predicting outcomes ahead of, or concurrent to, the course of human disease.

Cardiac Stem Cell Transplantation

After a heart attack, the patient is often left with a large amount of scar tissue in place of normally contracting heart muscle. If the amount of tissue is large enough, the patient's physical activity is limited and they may go on to chronic heart failure and death. Heart transplantation remains the treatment of choice, but the number of available organs will never meet more than a small fraction of the growing demand (17, 18). As another treatment option, stem cell therapy to regenerate the damaged heart is being aggressively pursued (19). The present invention has use to image, quantify and monitor the progression of transplanted stem cells from undifferentiated to differentiated states, as the cells repopulate the scar tissue with normally functioning heart tissue. The use of magnetosome-like structures, augmented by increased ferritin, to track the progress of tissue regeneration has both research and therapeutic applications.

a) Prior to transplantation, stem cells may be transfected with genes that produce magnetosome-like structures and HF and/or LF genes of the invention to follow the fate of the transplanted cells by MR imaging. This would follow the original stem cell population, from transplantation to lineage commitment and differentiation, by the combination of magnetosome-like structures and augmented ferritin storage.

To monitor the switch from proliferation to differentiation, cells would be transfected with magnetotactic bacterial, including magnetosome, and HF and/or LF constructs in which the promoter responds to stage-specific differentiation signals. This will indicate early and late events in stem cell differentiation and localize these events within the injured heart.

b) Different types of cellular differentiation may be monitored by transfecting stem cells with magnetotactic bacterial, including magnetosome, and HF and/or LF constructs of the invention that respond to transcription factors present in specific types of cardiac cells, such as smooth muscle cells, endothelial cells or myocytes. This will indicate the number of stem cells needed for successful treatment and how efficient stem cells are at producing functional myocardium.

c) The rate of stem cell loss after transplantation may also be monitored by placing magnetotactic bacterial, including magnetosome, and HF and/or LF genes behind promoters sensitive to cell death signals, including apoptosis, necrosis, autophagy and cornification (20). Alternatively, magnetotactic bacterial, including magnetosome, and HF and/or LF genes may be co-expressed with early markers of cell death. In this context, magnetosome-like structure formation and augmented ferritin storage protein would localize the extent of cell death that undermines stem cell therapy in a given organ.

Tracking Neurodegenerative Disease

Iron misregulation has been acknowledged in a number of diseases, including Alzheimer's disease (21). The Amyloid Precursor Protein (APP) has an IRE in the 5' untranslated region of the mRNA. The role of biometal dysregulation and oxidative stress in Aβ amyloid formation may be detected by the expression of magnetotactic bacterial, like MagA, including magnetosome, and HF and/or LF genes in neural cells.

a) Iron uptake may be monitored by the combination of magnetotactic bacterial, like MagA, including magnetosome, and HF and/or LF gene expression, which respond to iron supplementation. In this example, MagA and HF and/or LF are acting like a sensor of iron. MRI may be used to detect iron accumulation ahead of the amyloid plaque. The constructs and methods of the invention may also reveal the balance of IRE+/IRE− isoforms of key proteins in health and disease.

b) Changes in APP expression may be monitored using MRI by expression of the combination of magnetotactic bacterial genes, like MagA, including magnetosome, and HF and/or LF genes using vectors that respond to the APP promoter.

c) Potentially, therapies will be devised such that MagA and HF and/or LF remove cytotoxic iron by storing it in a safe form: as an iron biomineral in modified ferritin and/or a magnetosome-like structure.

d) New PET probes have recently been developed to Aβ amyloid and tau proteins to enable imaging of the onset and progression of Alzheimer's disease. This paves the way for PET/MRI in pre/clinical models of the disease. Magnetotactic bacterial, including MagA and magnetosome, and HF and/or LF gene expression in cells, tissues and animals can be now used for the purpose of PET/MR imaging in this disease.

Using Combinations of Magnetotactic and Mammalian Genes for Cell Tracking

The invention relates to the use of magnetotactic bacterial genes, including magnetosome genes, and mammalian genes, including the modified ferritin subunits, in combinations that augment or modulate MR contrast by regulating cellular iron biomineralization and/or the formation of magnetosome-like structures. These structures may generate all or part of the magnetosome, including modifications to iron uptake, iron biomineralization, iron compartmentalization and the arrangement of magnetosome-like structures within the cell.

a) MamJ and MamK are magnetosome proteins needed for the alignment of magnetosomes into a chain, connected to the cytoskeleton. Disruption of this interaction removes the chain-like structure and results in magnetosomes that are either dispersed or in clusters within the cytoplasm. Since each magnetosome normally constitutes a single magnetic domain, their arrangement within the cell will influence the MR contrast signal.

b) Regulatory proteins such as MamI may be used to dictate when the magnetosome-like structure will be properly synthesized (Kolinko, I., LohBe, A., Borg, S., Raschdorf, O., Jogler, C., Tu, Q., Posfai, M., Tompa, E., Plitzko, J., Brachmann, A., Wanner, G., Muller, R., Zhang, Y., and Schuler, D. (2014) Biosynthesis of magnetic nanostructures in a foreign organism by transfer of bacterial magnetosome gene clusters, *Nat Nanotechnol* 9, 193-197). In this way essential magnetosome genes may be used to regulate when and where the magnetosome-like structure will be expressed.

c) The iron biomineral in magnetosomes is partially regulated by Mms6. In this way, characteristics of the iron biomineral may be altered by select gene expression to influence the MR signal. Such regulation may include the size and composition of the biomineral, giving hematite, magnetite ($Fe_3O_4$), greigite ($Fe_3S_4$), or another biomineral.

d) Using select magnetotactic and mammalian genes to impart distinct magnetic signatures for MRI, changes in cellular activity may be tracked by expressing different combinations of these genes at different developmental stages. In this embodiment, the MR signal from a magnetosome-like structure appears at the onset of promoter stimulation by a given transcription factor. As that activity changes so does the MR signal. In addition, as new activities appear the MR signal may be modified again by genetically programming a different feature of the magnetosome-like structure to respond to these subsequent cellular factors. This strategy may be used to understand the factors that dictate a disease process, ahead of permanent tissue damage.

Magnetic Particle Imaging of Magnetosome-like Structures

Magnetic Particle Imaging (MPI) is an emerging area of MRI where nanoparticles of iron are non-invasively tracked and quantified (Saritas, E U, Goodwill, P W, Croft, L R, Konkle, J J, Lu, K, Zheng, B and Conolly, S M (2013) Magnetic Particle Imaging (MPI) for NMR and MRI Researchers. J Magn Reson 229, 116-126). Magnetosome-like structures can be used for MPI where genes from magnetotactic bacteria are co-expressed with mammalian genes to create the iron nanoparticles that have specific MPI signals Biomed Tech (Berl). 2013 Dec;58(6):493-507. doi: 10.1515/bmt-2012-0058.Tailoring the magnetic and pharmacokinetic properties of iron oxide magnetic particle imaging tracers. Ferguson R M, Khandhar A P, Arami H, Hua L, Hovorka O, Krishnan K M.

Co-expression of Human and Magnetotactic Bacterial Genes in Prokaryotes

Bacteria that live in the human gut may be genetically programmed to co-express magnetotactic bacterial genes, including magnetosome genes, and human genes, like the ferritin heavy and light subunits, to produce magnetosome-like structures.

a) In an aspect of the invention, these gut microbes may secrete therapeutic proteins to treat intestinal diseases and the magnetosome-like structures they harbour will permit non-invasive tracking of their location. Since this type of therapy may be stopped by flushing out the microbes with the use of laxatives, MRI can be used to verify the removal the magnetic bacteria.

b) In another aspect of the invention, gut bacteria may be engineered for production of magnetosome-like structures once a stimulatory signal is generated by the subject to initiate formation of the contrast agent in situ. The stimulatory agent may be endocrine, paracrine or autocrine. Furthermore, the combination of genes expressed may be programmed to give a unique magnetosome-like structure that depends on the nature of the stimulant.

c) Administration and monitoring of this therapy may be externally regulated. Gut microbes expressing a combination of magnetotactic bacterial and human genes to form magnetosome-like structures may be administered and allowed to migrate to the desired location in the GI tract, prior to activation of therapeutic gene expression by an oral antibiotic like tetracycline. This would ensure that the bacteria have reached the correct target along the intestine and minimize side effects elsewhere, such as in the stomach or bowel.

EXAMPLES

RT-PCR of MDA-MB-435 Cells Expressing MaqA and Modified Ferritin Subunits HF+LF (FIG. 1)

Transcripts were amplified from 1 µg of total RNA, isolated from stably-expressing cells (clone 12), by reverse transcription (RT). The polymerase chain reaction (PCR) was performed on 4 μl RT, using 60° C. for the annealing temperature and 35 cycles. Ethidium bromide staining of complimentary DNA (cDNA) separated on a 1% agarose gel shows the product amplified with MagA primers (lane 2, 650 bp), HF primers (lane 3, 450 bp), LF primers (lane 4, 500 bp) and α-actin primers (lane 5, 150 bp). Lane 6 contains an RT negative control for β-actin. Lane 1 contains a 1 Kb DNA ladder (Life Technologies).

TABLE 1

ICP-MS~ analysis of iron and zinc content in MDA-MB-435 cells expressing MagA and HF + LF

| Sample | [Protein]* (mg/ml) | [Fe] (μg/ml) | Amount of Fe/ Protein (μg/mg) | [Zn] (μg/ml) | Amount of Zn/ Protein (μg/mg) | Ratio of Fe/Zn |
|---|---|---|---|---|---|---|
| RIPA/ inhibitors‡ | 0 | 0 | ND | 0 | ND | ND |
| 1. Cells minus Fe | 1.00 | 0.029 | 0.029 | 0.108 | 0.108 | 0.273 |
| 2. Cells minus Fe | 1.00 | 0.038 | 0.038 | 0.112 | 0.112 | 0.342 |
| 3. Cells plus Fe 1 day | 1.00 | 0.341 | 0.341 | 0.115 | 0.115 | 2.969 |
| 4. Cells plus Fe 3 days | 1.00 | 0.471 | 0.471 | 0.123 | 0.123 | 3.835 |
| 5. Cells plus Fe 5 days | 1.00 | 0.510 | 0.510 | 0.085 | 0.085 | 5.973 |

~ICP-MS, Inductively-coupled plasma mass spectrometry
^ Stably-expressing cells (clone 12) were cultured in the presence (plus Fe) and absence (minus Fe) of medium supplemented with iron: 250 μM ferric nitrate.
*Protein was measured by the BCA assay: Smith et al. (1985) Anal. Biochem. 150, 76-85.
‡Cells were lysed in RIPA buffer (10 mM Tris-HCl pH 7.5/140 mM NaCl/1% NP-40/1% sodium deoxycholate/ 0.1% SDS) containing protease inhibitors (Complete Mini, Roche Diagnostic Systems).

TABLE 2

Transverse relaxation rates$^a$ in MDA-MB-435 cells co-expressing MagA and the modified ferritin subunits (HF + LF)

| Sample$^b$ | R2* | R2 |
|---|---|---|
| MagA + HF + LF | 13.65 ± 0.15 | 11.74 ± 0.64 |
| MagA + HF + LF + Fe | 14.07 ± 0.33 | 13.20 ± 0.50 |

$^a$Cells were mounted in spherical gelatin phantoms for measurement of relaxation rates at 3T following the method of Sengupta et al, 2014. Results are the average of 2 experiments.
$^b$Stably-expressing cells (clone 12) were cultured in the presence (+Fe) and absence of medium supplemented with iron: 250 μM ferric nitrate.

REFERENCES

1. Komeili, A. (2007) Molecular mechanisms of magnetosome formation, *Annu Rev Biochem* 76, 1-27.
2. Zurkiya, O., Chan, A. W., and Hu, X. (2008) MagA is sufficient for producing magnetic nanoparticles in mammalian cells, making it an MRI reporter, *Magn Reson Med* 59, 1225-1231.
3. Benoit, M., Mayer, D., Barak, Y., Chen, I., Hu, W., Cheng, Z., Wang, S., Spielman, D., Gambhir, S., and Matin, A. (2009) Visualizing implanted tumors in mice with magnetic resonance imaging using magnetotactic bacteria, *Clin Cancer Res* 15, 5170-5177.
4. Goldhawk, D., Rohani, R., Sengupta, A., Gelman, N., and Prato, F. (2012) Using the magnetosome to model effective gene-based contrast for magnetic resonance imaging, *WIRES Nanomed Nanobiotechnol Epub ahead of print*, doi: 10.1002/wnan.1165.
5. Goldhawk, D., Lemaire, C., McCreary, C., McGirr, R., Dhanvantari, S., Thompson, R., Figueredo, R., Koropatnick, J., Foster, P., and Prato, F. (2009) Magnetic resonance imaging of cells overexpressing MagA, an endogenous contrast agent for live cell imaging, *Mol Imaging* 8, 129-139.
6. Rohani, R., Figueredo, R., Bureau, Y., Koropatnick, J., Foster, P., Thompson, R., Prato, F., and Goldhawk, D. (2013) Imaging tumor growth non-invasively using expression of MagA or modified ferritin subunits to augment intracellular contrast for repetitive MRI, *Mol Imaging Biol, Epub ahead of print*, doi: 10.1007/s11307-11013-10661-11308.
7. Anderson, C., Shen, M., Eisenstein, R., and Leibold, E. (2012) Mammalian iron metabolism and its control by iron regulatory proteins, *Biochem Biophys Acta* 1823, 1468-1483.
8. Sengupta, A., Quiaoit, K., Thompson, R., Prato, F., Gelman, N., and Goldhawk, D. (2013) Biophysical features of MagA expression in mammalian cells: implications for MRI contrast, *Frontiers in Microbiotechnology, Ecotoxicology and Bioremediation*, submitted
9. Lee, C., Thompson, R., Prato, F., Goldhawk, D., and Gelman, N. (2013) Transverse relaxation rate (R2) dependence on refocusing pulse interval (2tau) in MagA expressing breast/melanoma tumor cells, In *World Molecular Imaging Conference*, Abstract LBAP 129, Savannah, USA.
10. Sengupta, A., Rohani, R., Thompson, R., Prato, F., Goldhawk, D., and Gelman, N.
(2012) MRI relaxation rates in tumour cells expressing the MagA reporter gene In *International Society for Magnetic Resonance in Medicine Scientific Workshop on MRI-based Cell Tracking*, Abstract 26, Miami, USA.
11. Liu, L., McGirr, R., Bondoc, A., Thompson, R., Prato, F., Goldhawk, D., and Hoffman, L. (2013) Non-Invasively Targeting Myocardial Progenitor Cells for the Treatment of Duchenne Muscular Dystrophy-Related Cardiomyopathy using MRI/PET, In *Stem Cell Network*, Abstract accepted, Banff, Canada.
12. Quiaoit, K., Koropatnick, J., Gelman, N., and Goldhawk, D. (2013) MagA Reporter Gene Expression for Magnetic Resonance Imaging of Breast Carcinoma, In *London Health Research Day*, Biomedical Imaging & Engineering Abstract 33, London, Canada.
13. Recalcati, S., Locati, M., Marini, A., Santambrogio, P., Zaninotto, F., De Pizzol, M., Zammataro, L., Girelli, D., and Cairo, G. (2010) Differential regulation of iron homeostasis during human macrophage polarized activation, *Eur J Immunol* 40, 824-835.

14. Pantopoulos, K., Porwal, S., Tartakoff, A., and Devireddy, L. (2012) Mechanisms of mammalian iron homeostasis, *Biochemistry* 51, 5705-5724.

15. Braun, R. (2013) When harmless bacteria go bad, *Scienfific American.*

16. Ghajar, C., Peinado, H., Mori, H., Matei, I., Evason, K., Brazier, H., Almeida, D., Koller, A., Najjar, K., Stainier, D., Chen, E., Lyden, D., and Bissell, M. (2013) The perivascular niche regulates breast tumour dormancy, *Nat Cell Biol* 15, 807-817.

17. IHME, and Cohen, J. (2012) Health metrics. A controversial close-up of humanity's health, *Science* 338, 1414-1416.

18. News. (2013) World Disease by the Numbers, *Science* 341, 325.

19. Makkar, R., Smith, R., Cheng, K., Malliaras, K., Thomson, L., Berman, D., Czer, L., Marban, L., Mendizabal, A., Johnston, P., Russell, S., Schuleri, K., Lardo, A., Gerstenblith, G., and Marban, E. (2012) Intracoronary cardiosphere-derived cells for heart regeneration after myocardial infarction (CADUCEUS): a prospective, randomised phase 1 trial, *Lancet* 379, 895-904.

20. Kroemer, G., Galluzzi, L., Vandenabeele, P., Abrams, J., Alnemri, E., Baehrecke, E., Blagosklonny, M., EI-Deiry, W., Golstein, P., Green, D., Hengartner, M., Knight, R., Kumar, S., Lipton, S., Malorni, W., Nuñez, G., Peter, M., Tschopp, J., Yuan, J., Piacentini, M., Zhivotovsky, B., and Melino, G. (2009) Classification of cell death: recommendations of the Nomenclature Committee on Cell Death 2009, *Cell Death Differ* 16, 3-11.

21. Huang, X., Moir, R., Tanzi, R., Bush, A., and Rogers, J. (2004) Redox-active metals, oxidative stress, and Alzheimer's disease pathology, *Ann NY Acad Sci* 1012, 153-163.

22. Ferguson R M, Khandhar A P, Arami H, Hua L, Hovorka O, Krishnan K M.Biomed Tech (Berl). 2013 Dec; 58(6):493-507. doi: 10.1515/bmt-2012-0058. Tailoring the magnetic and pharmacokinetic properties of iron oxide magnetic particle imaging tracers.

Although the present invention and its advantages have been described in detail, it should be understood that various changes, substitutions and alterations can be made herein without departing from the scope of the invention as defined by the appended claims. Moreover, the scope of the present application is not intended to be limited to the particular embodiments of the process, composition of matter, means, methods and steps described in the specification.

We claim:

1. An expression system for augmenting and/or regulating iron levels in cells, said expression system comprising (a) a complete or partial bacterial MamAB operon comprising magnetotactic genes to amplify iron uptake, compartmentalization and biomineralization in cells, and (b) one or more genes each encoding one or more eukaryotic ferritin subunits, the one or more genes lacking an iron responsive element (IRE), wherein (a) and (b) are under control of one or more promoters and, optionally, one or more selection markers.

2. The expression system of claim 1 wherein said one or more eukaryotic ferritin subunits are mammalian.

3. The expression system of claim 1, wherein the one or more eukaryotic ferritin subunits comprise both a ferritin heavy subunit and a ferritin light subunit.

4. The expression system of claim 1, wherein said cells are eukaryotic.

5. A cell transformed with the expression system of claim 1.

6. The cell of claim 5, wherein said cell is detected using an imaging system selected from the group consisting of positron emission tomography (PET), magnetic resonance imaging (MRI), gamma-ray imaging camera (GREI-II), computed tomography (CT), Single photon emission computed tomography (SPECT), bioluminescence tomography (BLT), magnetic particle imaging (MPI) and combinations thereof.

7. A method of augmenting and/or regulating iron levels in cells and subsequent detection of the cells, the method comprising utilizing the expression system of claim 1 to co-express said magnetotactic bacterial genes from said MamAB operon and said one or more eukaryotic ferritin subunits to form a magnetosome-like structure containing augmented amounts of iron therein; and detecting the cells using an imaging system selected from the group consisting of positron emission tomography (PET), magnetic resonance imaging (MRI), gamma-ray imaging camera (GREI-II), computed tomography (CT), Single photon emission computed tomography (SPECT), bioluminescence tomography (BLT), magnetic particle imaging (MPI) and combinations thereof.

8. The method of claim 7 for use in one or more of the following:
- detecting changes in cellular iron;
- tracking cancer growth and metastasis;
- image, quantify and/or monitor progression of transplanted stem cells;
- tracking neurodegenerative disorders; and
- cell tracking in vivo.

* * * * *